(12) United States Patent
Sakaguchi et al.

(10) Patent No.: US 9,592,164 B2
(45) Date of Patent: Mar. 14, 2017

(54) OPEN-TYPE DISPOSABLE DIAPER WITH CROTCH STRETCH UNIT

(71) Applicant: UNICHARM CORPORATION, Shikokuchuo-shi, Ehime (JP)

(72) Inventors: Satoru Sakaguchi, Kanonji (JP); Kana Sawa, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 14/377,012

(22) PCT Filed: Feb. 4, 2013

(86) PCT No.: PCT/JP2013/052445
§ 371 (c)(1),
(2) Date: Aug. 6, 2014

(87) PCT Pub. No.: WO2013/118668
PCT Pub. Date: Aug. 15, 2013

(65) Prior Publication Data
US 2015/0011959 A1  Jan. 8, 2015

(30) Foreign Application Priority Data
Feb. 7, 2012  (JP) .................................. 2012-024547

(51) Int. Cl.
*A61F 13/49*  (2006.01)
*A61F 13/53*  (2006.01)
(Continued)

(52) U.S. Cl.
CPC ........ *A61F 13/49017* (2013.01); *A61F 13/49* (2013.01); *A61F 13/49001* (2013.01);
(Continued)

(58) Field of Classification Search
CPC ................ A61F 13/49; A61F 13/49001; A61F 13/49009; A61F 13/49011; A61F 13/49017;
(Continued)

(56) References Cited

U.S. PATENT DOCUMENTS 4,685,916 A    8/1987 Enloe
4,935,021 A *  6/1990 Huffman ............. A61F 13/5323
                                          604/385.26
(Continued)

FOREIGN PATENT DOCUMENTS

DE   202011000820     *  9/2011  ........ A61F 13/49011
DE   202011000820 U1    9/2011
(Continued)

OTHER PUBLICATIONS

Office Action issued Mar. 9, 2015, corresponding to Chinese patent application No. 201380008302.7.
(Continued)

*Primary Examiner* — Kathryn E Ditmer
(74) *Attorney, Agent, or Firm* — Hauptman Ham, LLP (57) ABSTRACT

An open-type disposable diaper includes a crotch stretch unit formed in an absorber arrangement region where an absorber is arranged in a crotch region and being stretchable in a product longitudinal direction; a pair of leg stretch units formed along a leg hole openings and being stretchable in at least the product longitudinal direction; and a waist stretch unit formed in a back waistline region and being stretchable in a product widthwise direction; the absorber core arrangement region enclosed by the crotch stretch unit, the leg stretch units, and the waist stretch unit and configuring the absorber is formed so as not to be stretched. The length of the absorber core arrangement region in the product longitudinal direction is configured to be longer than half the
(Continued)

length of the crotch stretch unit in the product longitudinal direction.

10 Claims, 6 Drawing Sheets

(51) Int. Cl.
   *A61F 13/494* (2006.01)
   *A61F 13/532* (2006.01)
(52) U.S. Cl.
   CPC ...... *A61F 13/49413* (2013.01); *A61F 13/532* (2013.01); *A61F 13/5323* (2013.01); *A61F 2013/49031* (2013.01); *A61F 2013/49046* (2013.01); *A61F 2013/49063* (2013.01); *A61F 2013/5326* (2013.01); *F04C 2270/0421* (2013.01)
(58) Field of Classification Search
   CPC . A61F 13/49031; A61F 13/532; A61F 13/533
   See application file for complete search history.

(56) References Cited

U.S. PATENT DOCUMENTS

| | | | |
|---|---|---|---|
| 5,649,919 A | | 7/1997 | Roessler et al. |
| 6,090,090 A | * | 7/2000 | Roe ................ A61F 13/493 604/385.21 |
| 6,409,715 B1 | * | 6/2002 | Tanji ............... A61F 13/495 604/385.01 |
| 7,827,623 B2 | * | 11/2010 | Kurata ............... A41B 9/00 2/400 |
| 7,972,319 B2 | * | 7/2011 | Umebayashi ........ A41B 9/001 156/150 |
| 2005/0096624 A1 | * | 5/2005 | Hoshino .......... A61F 13/49019 604/385.27 |
| 2007/0239128 A1 | * | 10/2007 | Takada ............. A61F 13/495 604/385.25 |
| 2012/0143162 A1 | * | 6/2012 | Mukai ............ A61F 13/15804 604/385.3 |
| 2013/0102982 A1 | * | 4/2013 | Nakano .......... A61F 13/49019 604/365 |
| 2013/0267924 A1 | * | 10/2013 | Mukai ............. A61F 13/533 604/374 |

FOREIGN PATENT DOCUMENTS

| | | | |
|---|---|---|---|
| EP | 1072243 A2 | | 1/2001 |
| EP | 1875819 A1 | | 1/2008 |
| EP | 2832332 A1 | | 2/2015 |
| EP | 2835116 A1 | | 2/2015 |
| EP | 2901982 A1 | | 8/2015 |
| JP | 63-11151 A | | 1/1988 |
| JP | 2003-070840 A | | 3/2003 |
| JP | 2006-271898 A | | 10/2006 |
| JP | 2006271898 A | * | 10/2006 |
| JP | 2008-136515 A | | 6/2008 |
| JP | 2008-525100 A | | 7/2008 |
| JP | 2008-253289 A | | 10/2008 |
| JP | 2008253289 A | * | 10/2008 |
| JP | 2010-279612 A | | 12/2010 |
| JP | 2011-193971 A | | 10/2011 |
| JP | 2011-250966 A | | 12/2011 |
| JP | 2012-24547 A | | 2/2012 |
| TW | 201108998 A | | 3/2011 |
| WO | 2006/118214 A | | 11/2006 |
| WO | WO 2010140678 A1 | * | 12/2010 ....... A61F 13/15804 |
| WO | 2014/073636 A1 | | 5/2014 |

OTHER PUBLICATIONS

International Search Report mailed May 7, 2013 in International Application No. PCT/JP2013/052445, with English language translation.
Office Action mailed Jul. 21, 2015, corresponding to Japanese patent application No. 2013-116882.
Office Action in TW application No. 102103320, dated Jun. 14, 2016.
Office Action in Eurasian application No. 201400815, mailed Mar. 22, 2016.
Extended European Search Report in EP Application No. 13747286. 6, dated Sep. 8, 2015.
Office Action in EA Application No. 201400815, issued Sep. 28, 2016.
Office Action in AU Application No. 2013218941, issued Dec. 1, 2016.

* cited by examiner

OPEN-TYPE DISPOSABLE DIAPER WITH CROTCH STRETCH UNIT

RELATED APPLICATIONS

The present application is a National Phase of International Application Number PCT/JP2013/052445, filed Feb. 4, 2013, which claims priority to Japanese Application Number 2012-024547, filed Feb. 7, 2012.

TECHNICAL FIELD

The present invention relates to an open-type disposable diaper.

BACKGROUND ART

Conventionally, there is known an open-type disposable diaper which has a front waistline region, a back waistline region, and a crotch region, a pair of leg hole openings, and an absorber spanning the crotch region and extending to the front waistline region and back waistline region (for example, see Patent Literature 1).

CITATION LIST

Patent Literature

[PTL 1]
Japanese Unexamined Patent Application Publication No. 2003-70840

SUMMARY OF INVENTION

However, in the recent years, due to the trend towards nuclear families and a reduction in birth rate, there has been an increase in mothers who do not have any experience of putting diapers on infants and toddlers, and as a result, the mothers are expressing their voices that they do not know at what position of the wearer the above-mentioned open-type disposable diaper needs to be worn.

In response thereto, manufacturers have started explaining the detailed procedure of how to wear an open-type disposable diaper by way of various means such as stores and the Internet.

Given the current situation, the applicant has come to realize that there is a high need in the market for a disposable diaper with which it is possible to easily and sensuously understand at what position of the open-type disposable diaper the wearer needs to be pulled in or lifted up without a need of reading the procedure of how to wear the diaper.

Thus, the present invention has been achieved in view of the above problem, and an object thereof is to provide an open-type disposable diaper that can be easily and correctly worn by a wearer.

A first characteristic of the present invention is summarized as an open-type disposable diaper including: a front waistline region; a back waistline region; a crotch region positioned between the front waistline region and the back waistline region; a pair of leg hole openings; an absorber spanning the crotch region and extending to the front waistline region and back waistline region; a product longitudinal direction from the front waistline region towards the back waistline region; and a product widthwise direction perpendicular to the product longitudinal direction, wherein the open-type disposable diaper further includes: a crotch stretch unit formed in an absorber arrangement region where the absorber is arranged in the crotch region and being stretchable in the product longitudinal direction; a pair of leg stretch units formed along the leg hole openings and being stretchable in at least the product longitudinal direction; and a waist stretch unit formed in the back waistline region and being stretchable in the product widthwise direction; the absorber core arrangement region enclosed by the crotch stretch unit, the leg stretch units, and the waist stretch unit and configuring the absorber is formed so as not to be stretched; and a length of the absorber core arrangement region in the product longitudinal direction is configured to be longer than half the length of the crotch stretch unit in the product longitudinal direction.

DESCRIPTION OF EMBODIMENTS

First Embodiment of the Present Invention

With reference to FIG. 1 through FIG. 6, an open-type disposable diaper 10 according to a first embodiment of the present invention will be described.

In the following description of the drawings, the same or similar reference numerals are used to designate the same or similar portions. It will be appreciated that the drawings are schematically shown and the ratio and the like of each dimension are different from the real ones.

Accordingly, specific dimensions should be determined in consideration of the explanation below. Moreover, among the drawings, the respective dimensional relations or ratios may differ.

Figure 1:
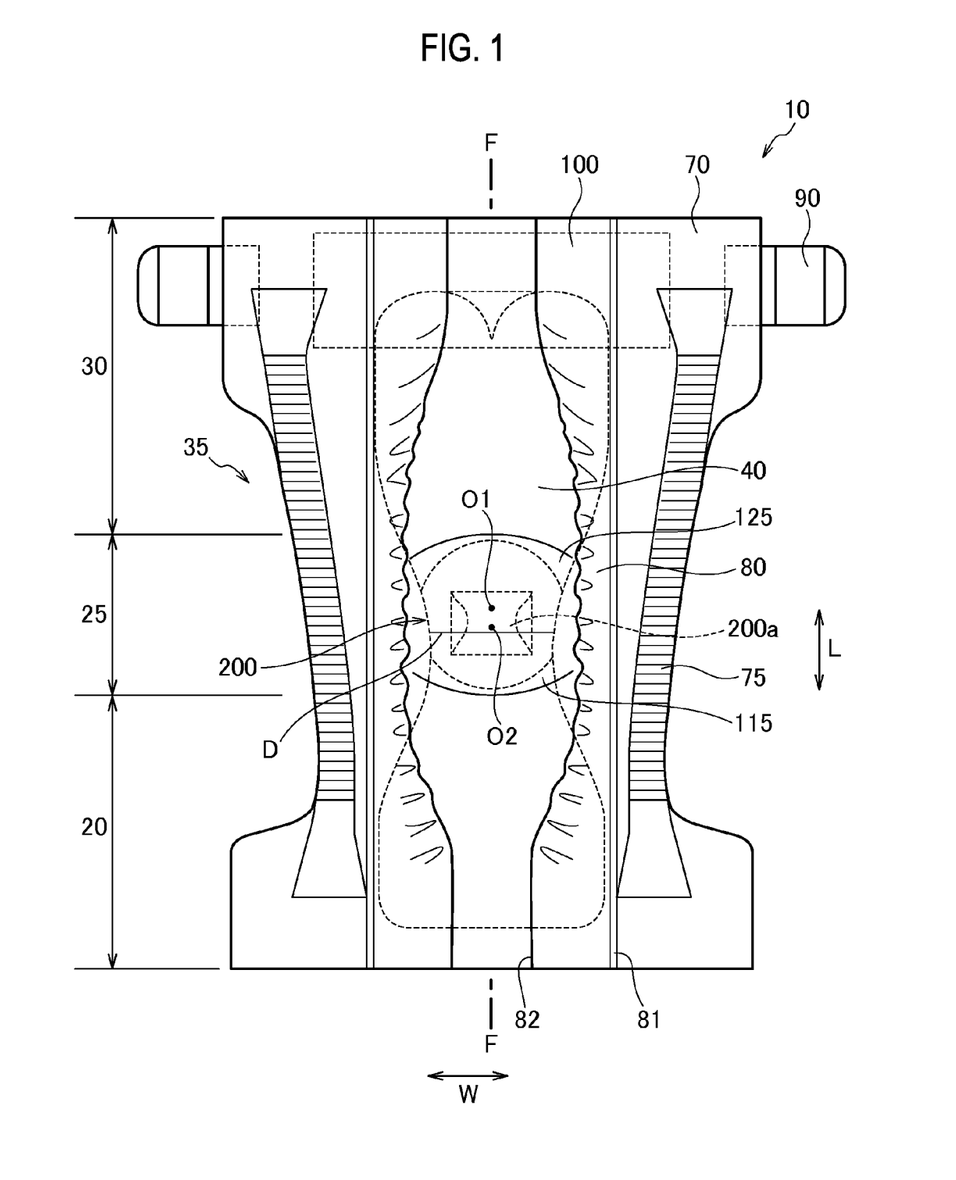
FIG. 1 is an exploded plan view of an open-type disposable diaper according to an embodiment of the present invention.
Figure 2:
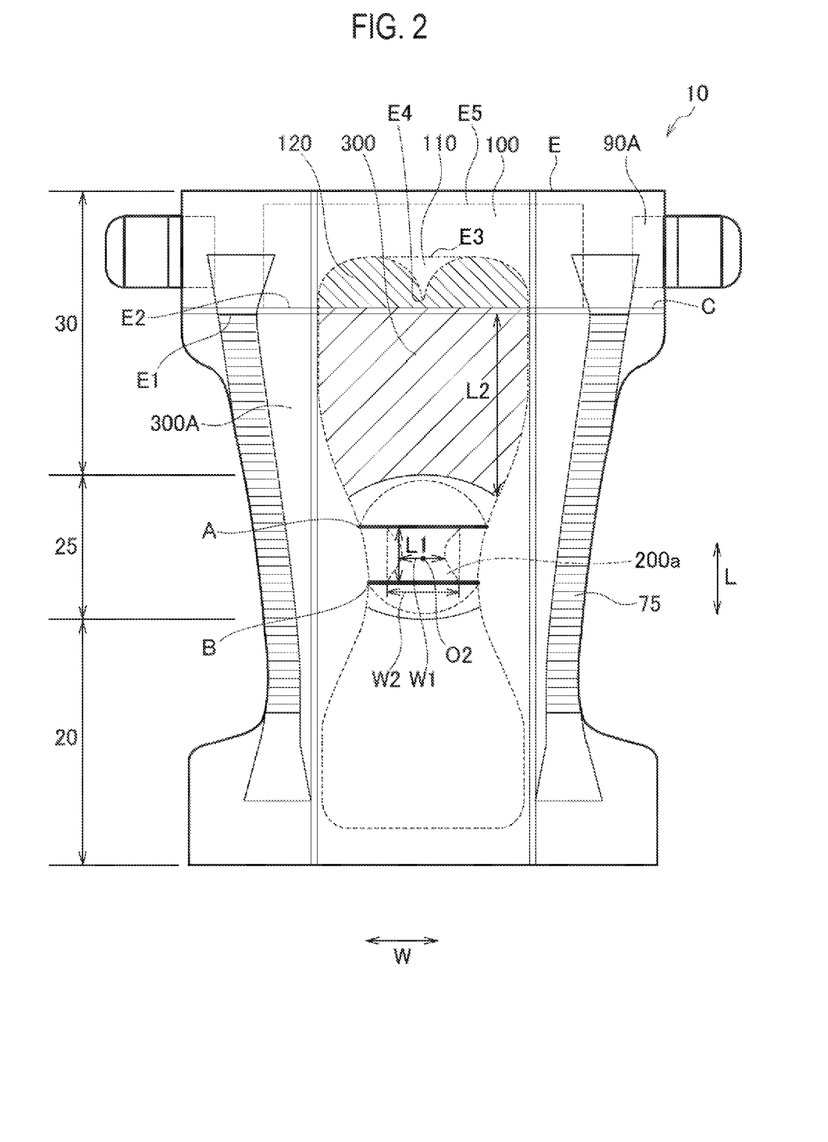
FIG. 2 is an exploded plan view of an open-type disposable diaper according to an embodiment of the present invention.
Figure 3:
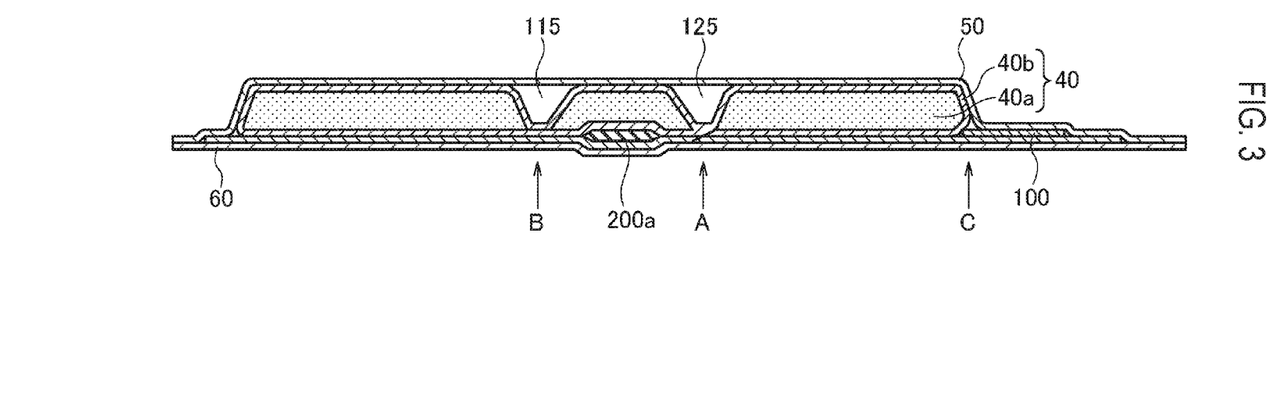
FIG. 3 is a diagram of an F-F cross section of an open-type disposable diaper according to a first embodiment of the present invention.

FIG. 1 and FIG. 2 are exploded plan views of the open-type disposable diaper 10 according to the present embodiment. FIG. 3 is a cross-sectional view of the open-type disposable diaper 10 along the F-F line illustrated in FIG. 1.

It must be noted that the exploded plan view of FIG. 1 is a diagram in which leg gathers 75 and leg side gathers 80 are in an elongated state such that wrinkles are not formed in a topsheet 50 and side sheets 70 that configure the disposable diaper, but for the sake of description, the leg side gathers 80 are illustrated in a stretched state.

As illustrated in FIG. 1 and FIG. 2, the open-type disposable diaper 10 includes a front waistline region 20, a crotch region 25, and a back waistline region 30. Furthermore, a pair of leg hole openings are formed in the open-type disposable diaper 10.

Here, the front waistline region 20 is the portion that is in contact with the front waistline portion of the wearer, the back waistline region 30 is the portion that is in contact with a back waistline portion of the wearer, and the crotch region 25 is the portion positioned between the front waistline region 20 and the back waistline region 30.

In the present embodiment, the direction from the front waistline region 20 towards the back waistline region 30 is called the product longitudinal direction L, and the direction perpendicular to the product longitudinal direction L is called the product widthwise direction W.

The open-type disposable diaper 10 includes an absorber 40 spanning the crotch region 25 and extending in the front waistline region 20 and the back waistline region 30. As illustrated in FIG. 3, the absorber 40 is configured from an absorber core 40a and a core wrap 40b.

The absorber core 40a is same as in the conventional disposable diaper, and can be configured appropriately by using popular components and materials, such as ground pulp and high absorbent polymer. The absorber core 40a is wrapped by the sheet-like core wrap 40b.

The core wrap 40b is a sheet for wrapping the absorber core 40a. A part of at least the skin surface contact side of the core wrap 40b is configured by various fibrous nonwoven fabrics or a tissue sheet having liquid-permeability.

For example, an air-through fibrous nonwoven fabric, a spunbond nonwoven fabric, or an SMS (spunbond—Meltblown—spunbond) nonwoven cloth having a mass of approximately 10 to 30 g/m$^2$, or a tissue sheet having a mass of approximately 10 to 30 g/m$^2$ can be used as the component configuring the core wrap 40b.

Furthermore, as illustrated in FIG. 3, the liquid-permeable topsheet 50 is provided at the top side (skin contact surface side) of the absorber 40, and a liquid-impermeable backsheet 60 is provided at the back side (non-skin contact surface side) of the absorber 40. A side flap 70 is provided at each side edge in the product widthwise direction W of the absorber 40. The side flaps 70 are made of one or two or more pieces of nonwoven fabrics overlapping one another.

Furthermore, a fastening tape 90 is provided in each of the pair of side flaps 70 in the back waistline region 30. The fastening tape 90 is configured to be mountable in a predetermined region at the non-skin contact surface side of the front waistline region 20.

The open-type disposable diaper 10 includes a crotch stretch unit 200a formed in the crotch region 25 and being stretchable in the product longitudinal direction L.

Specifically, the crotch stretch unit 200a is arranged in the crotch unit 200 formed in the crotch region 25. More specifically, the crotch stretch unit 200a is formed in an absorber arrangement region 300 where the absorber 40 is arranged in the crotch region 25.

Furthermore, the center of the crotch stretch unit 200a in the product longitudinal direction L is arranged at the side of the front waistline region 20 from the center of the open-type disposable diaper 10 in the product longitudinal direction L. However, the crotch stretch unit 200a is arranged to span the center of the open-type disposable diaper 10 in the product longitudinal direction L.

In the present embodiment, the crotch stretch unit 200a is configured from a stretchable sheet. For example, a stretch film formed by melting a thermoplastic elastomer resin, such as urethane and styrene, and then converting into the shape of a film, a stretchable nonwoven fabric formed from such stretchable fibers, or a composite sheet formed by pasting together inextensible sheets that have been partially cut into a stretchable film and stretchable nonwoven fabric, or have been made fragile can be used as the stretchable sheet.

Furthermore, rather than the stretchable sheet, the crotch stretch unit 200a may also be configured through an alternate, parallel arrangement of thread-like or stripe-like stretchable elastic members made from polyurethane elastic fibers and natural rubber.

In such a case, in view of the rigidity of the absorber core 40a and the rigidity of other members configuring the open-type disposable diaper 10, the thickness of the elastic members and the arrangement pitch can be selected appropriately, however, when the main body of the open-type disposable diaper 10 is in the natural state (unextended state), the entire side edge in the product widthwise direction W of the absorber core 40a is preferable to be in a contracted state.

Specifically, the ratio of expansion and contraction of the crotch stretch unit 200a is preferably 1.2 times to 1.8 times. For example, in the present embodiment, the ratio of expansion and contraction of the crotch stretch unit 200a may be set to 1.4 times.

The ratio of expansion and contraction implies the extent of expansion and contraction of the crotch stretch unit 200a in the stretching direction (product longitudinal direction L in the present embodiment), and is stipulated as below:

Ratio of expansion and contraction=(Length in the stretching direction of the crotch stretch unit 200a in the maximum extended state)/(Length in the stretching direction of the crotch stretch unit 200a in the natural state)

It should be noted that the ratio of expansion and contraction as used herein is to be measured as described below, for example.

Firstly, if the open-type disposable diaper 10 is inserted in a package, for example, then the open-type disposable diaper 10 is taken out of the package, and the diaper is kept in such a condition for 60 minutes in an ambient atmosphere having a temperature of 20° C.±2° C., and a relative humidity of 60%±5% RH.

Secondly, the length in the stretching direction of the desired region of the open-type disposable diaper in this state (that is, in the natural state), and the length in the stretching direction of the desired region, when the open-type disposable diaper is extended from its natural state until wrinkles caused by the elastic members are not visible, are measured.

By thus setting the ratio of expansion and contraction of the crotch stretch unit 200a to 1.2 times to 1.8 times, it is possible to favorably follow the stretching of the skin of the wearer.

For example, when the wearer is slouchy such that the front side of the body is cringing, the skin at the side of the hip portion of the wearer stretches by approximately 30% as compared to the state when the body has been stretched out.

That is, when the ratio of expansion and contraction of the crotch stretch unit 200a is 1.2 times or less, the contraction of the crotch stretch unit 200a in the natural state of the open-type disposable diaper is insufficient, and as compared to the case when the crotch stretch unit 200a has not been provided, the difference in the ease of curving of the open-type disposable diaper 10 is small because of which the front waistline region 20 does not rise at the desired position.

On the other hand, when the ratio of expansion and contraction of the crotch stretch unit 200a is more than 1.8 times, the contraction size in the contraction direction of the crotch stretch unit 200a becomes too large, because of which the region where the crotch stretch unit 200a exists easily comes in close contact with the body of the wearer rather than running along it, and the open-type disposable diaper 10 easily shifts to the lower side of the wearer.

The top side (topsheet 50 side) of the absorber 40 is formed along the leg hole openings 35, and a pair of stretchable leg stretch units (leg gathers) 75 are provided in at least the product longitudinal direction L.

The leg stretch units 75 are configured to be longer than the crotch stretch unit 200a in the product longitudinal direction L, and are provided at the outer side from the crotch stretch unit 200a in the product widthwise direction W.

Furthermore, same as the crotch stretch unit 200a, the leg stretch units 75 are formed from a stretchable sheet. Specifically, the width (the width in the product widthwise direction W in the natural state of the open-type disposable diaper 10) of the stretchable sheet is preferably 5 mm to 35 mm, in at least the crotch region 25.

Here, when the width of the stretchable sheet is less than 5 mm, the effect of the sheet running, substantially on its surface, along the area around the legs of the wearer is not exhibited, and when the width of the stretchable sheet exceeds 35 mm, the region along the area around the legs widens as a result of which the stretchable sheet may easily shift in towards the body of the wearer or may fold over.

The ratio of expansion and contraction of the leg stretch units 75 is preferably 1.5 times to 2.4 times. For example, in the present embodiment, the ratio of expansion and contraction of the leg stretch units 75 may be set to 1.9 times. The ratio of expansion and contraction of the leg stretch units 75 is stipulated in the same manner as the ratio of expansion and contraction of the above-mentioned crotch stretch unit 200a.

Furthermore, the interval between the inner ends of the pair of the left-right leg stretch units 75 in the product widthwise direction W widens from the crotch region 25 towards the front waistline region 20, and also widens from the crotch region 25 towards the back waistline region 30.

The interval is obtained by measuring the distance between the inner ends of the pair of the left-right leg stretch units 75 in the product widthwise direction W, after the open-type disposable diaper 10 is stretched in the product longitudinal direction L and the product widthwise direction W from the natural state until the state where wrinkles cannot be visually confirmed, and retained in that state.

Furthermore, the open-type disposable diaper 10 includes a waist stretch unit (waist gathers) 100 formed in the back waistline region 30 and being stretchable in the product widthwise direction W.

In the present embodiment, same as the crotch stretch unit 200a and the leg stretch units 75, the waist stretch unit 100 is configured from a stretchable sheet. The member configuring the waist stretch unit 100 is not particularly restricted, but a member that is as thin as possible with a low rigidity, and has a small reduction in width is preferably used.

In the present embodiment, a stretch film having a basis weight of 30 g/m$^2$ is used as the waist stretch unit 100. The stretch film is preferably used from the viewpoint of reducing the basis weight.

After being extended up to 1.5 to 2.5 times the length in the non-elongated state (natural state), the waist stretch unit 100 is adhered onto the backsheet 60 with a hot-melt adhesive or heat processing.

The waist stretch unit 100 is arranged between the topsheet 50 and the backsheet 60. As illustrated in FIG. 3, the core wrap 40b is arranged between the topsheet 50 and the waist stretch unit 100.

Alternatively, when an exterior sheet 60a arranged between the absorber 40 and the backsheet 60 has been provided, the waist stretch unit 100 may be arranged between the exterior sheet 60a and the backsheet 60.

Furthermore, when a leakage-preventing sheet is arranged intermittently in the product longitudinal direction L, the waist stretch unit 100 may perform the role of a leakage-preventing member. In such a case, the width of the waist stretch unit 100 is preferably more than the width of the absorber 40.

Furthermore, the waist stretch unit 100 may be configured such that when the waist stretch unit 100 is contracted in the product widthwise direction W, the width reduction rate in the product longitudinal direction L becomes 30% or less.

By setting the width reduction rate of the waist stretch unit 100 to 30% or less, and preferably to 10% or less, the contraction of the waist stretch unit 100 in the product longitudinal direction L is controlled, and even when the waist stretch unit 100 is arranged in the hip portion, the shifting of the ends of the back waistline region 30 from the predetermined position due to the contraction of the product longitudinal direction L can be controlled.

It should be note that the width reduction rate as used herein is to be measured as described below, for example.

Firstly, the waist stretch unit 100 is taken out from the open-type disposable diaper 10, the waist stretch unit 100 that has been taken out is kept in an ambient atmosphere having a temperature of 20° C.±2° C., and a relative humidity of 60%±5% RH for 24 hours, and then the width of the position corresponding to the center in the product widthwise direction W during the arrangement of the waist stretch unit 100 in the open-type disposable diaper 10 is set to the sheet-like elastic element width (WA) in the natural state.

Secondly, the entire width of the waist stretch unit 100 that has been taken out is held between the measuring chuck of the tensile testing machine (Autograph manufactured by Shimadzu Corporation), elongated the waist stretch unit 100 up to the width at the time of pasting to the open-type disposable diaper 10 at a speed of 100 mm/min., and then the width (WB) at the position corresponding to the center in the product widthwise direction W of the waist stretch unit 100 during the arrangement in the open-type disposable diaper 10 is measured.

Now, the measured (WA) and (WB) are used to calculate the width reduction rate with the expression described below.

$$\text{Width reduction rate (\%)}=((WA)-(WB))/(WA))\times 100$$

Furthermore, the absorber core arrangement region 300 is formed so as not to stretch. The absorber core arrangement region 300 is enclosed by the crotch stretch unit 200, the leg stretch unit 75, and the waist stretch unit 100, and is the region where the absorber core 40a configuring the absorber 40 is arranged.

The "predetermined region does not stretch" used herein implies that both the ratio of expansion and contraction of the predetermined region along the product longitudinal direction L and the ratio of expansion and contraction of the predetermined region along the product widthwise direction W is 1.15 times or less.

When the ratio of expansion and contraction of the absorber core arrangement region 300 is 1.15 times or less, wrinkles or ruggedness resulting from the contraction of the absorber core 40a do not occur substantially in the absorber core arrangement region 300, and the absorber core arrangement region 300 does not rise but can be maintained in a state close to the plane surface.

The absorber 40 includes low rigidity regions 115 and 125, where the basis weight is low or the absorber core 40a does not exist, along the ends in the product longitudinal direction L of the front waistline region 20 and the back waistline region 30 of the crotch stretch unit 200a, that is, along the ends in the product longitudinal direction L of the crotch unit 200.

Figure 4:
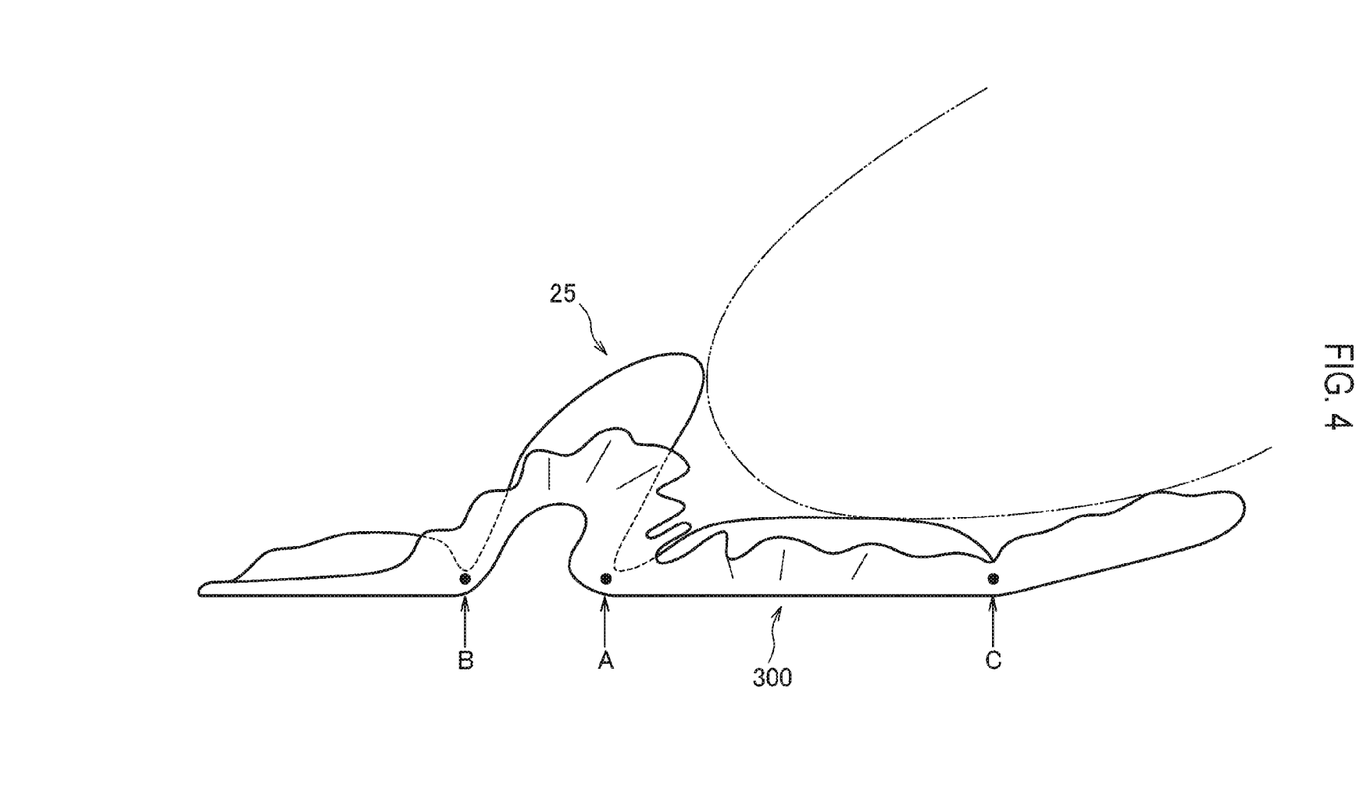
FIG. 4 is a diagram illustrating a state in which the open-type disposable diaper according to the first embodiment of the present invention is worn by the wearer.
Figure 6:
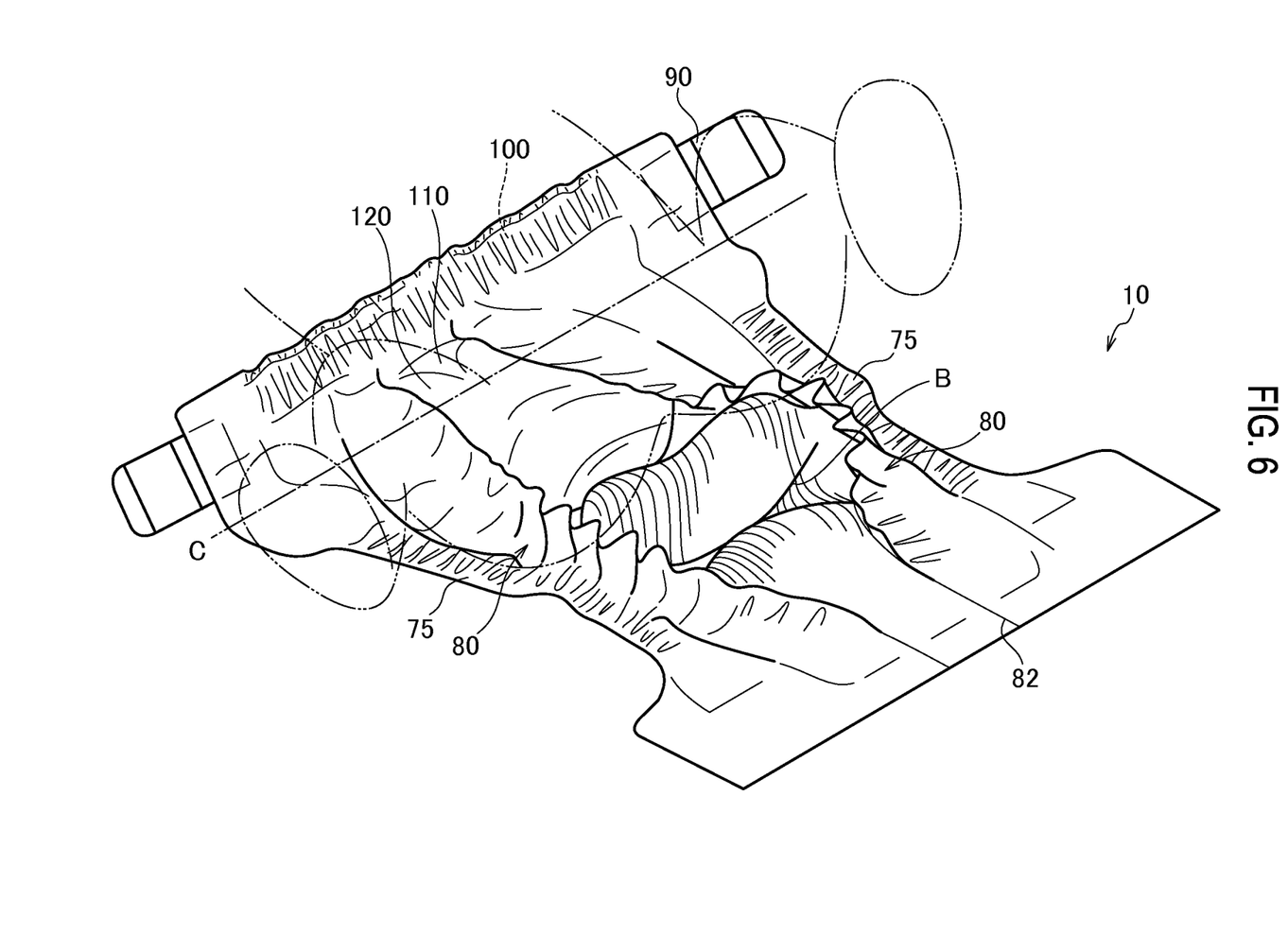
FIG. 6 is a diagram illustrating a state in which the open-type disposable diaper according to the first embodiment of the present invention is worn by the wearer.

According to the above configuration, as illustrated in FIG. 4 and FIG. 6, in an expanded open-type disposable diaper 10 in the natural state, the crotch region 25 can rise with a region A along the ends in the product longitudinal direction L at the side of the back waistline region 30 of the crotch stretch unit 200a, and a region B along the ends of the product longitudinal direction L at the side of the front waistline region 20 of the crotch stretch unit 200a as the base points.

Furthermore, as illustrated in FIG. 2, an end E1 at the side of the back waistline region 30 of the leg stretch units 75 is configured to be arranged at the side of the front waistline region 20 from an end E2 at the side of the crotch region 25 in the product longitudinal direction L of the waist stretch unit 100.

According to the above configuration, as illustrated in FIG. 4 and FIG. 6, a part of the back waistline region 30 can rise with a region C between the end E1 at the side of the back waistline region 30 in the product longitudinal direction L of the leg stretch units 75, and the end E2 at the side of the crotch region 25 in the product longitudinal direction L of the waist stretch unit 100 as the base point.

Furthermore, as illustrated in FIG. 2, the absorber core 40a is not arranged in a region 300A between the leg stretch units 75 and a joining portion 81.

According to the above configuration, as a result of the existence of the region 300A, the absorber core arrangement region 300 does not easily get affected by the rise of the leg stretch units 75, and is easily maintained in a state close to the plane surface.

Furthermore, as illustrated in FIG. 2, the length L2 of the absorber core arrangement region 300 in the product longitudinal direction L is configured to be longer than half the length L1 of the crotch stretch unit 200a in the product longitudinal direction L.

According to the above configuration, the wearing assistant of the diaper can visually confirm the absorber core arrangement region 300 that is maintained in a state close to the plane surface as the reference position where the wearer must be placed in the expanded open-type disposable diaper 10 in the natural state.

Furthermore, a pair of leg side gathers 80 extending along the product longitudinal direction L are provided at the inner side of the pair of leg stretch units 75 (towards the center in the product widthwise direction W).

The leg side gathers 80 include a joining portion 81, and a free end portion 82 positioned at the opposite side of the joining portion 81 and provided with an elastic member (not shown in the figure).

The joining portion 81 may be joined with the topsheet 50, or may be joined with a leakage-preventing film or the backsheet 60 arranged at the non-skin contact surface side from the topsheet 50.

Furthermore, the ends in the product longitudinal direction L of the free end portion 82 are joined with the topsheet 50. The joining portion 81 is arranged between the crotch stretch unit 200a and the leg stretch unit 75, in the product widthwise direction W.

As for the leg side gathers 80, when the diaper is worn, the joining portion 81 rises up as the proximal end and the free end portion 82 is in contact with the skin of the wearer as the apex.

It must be noted that in the back waistline region 30 from the crotch unit 200, the length between the joining portion 81 and the free end portion 82 is configured to be shorter than the length between the joining portion 81 and the leg stretch units 75.

According to the above configuration, at the central side (side of the absorber core arrangement region 300) in the product widthwise direction W from the leg stretch units 75 that have risen up, the leg side gathers 80 rise up, and the height of rise of the leg side gathers 80 is configured to be lower than the height of rise of the leg stretch units 75, making it easier for the wearing assistant to focus on the absorber core arrangement region 300.

Furthermore, the absorber 40 includes a low rigidity region 110, where the basis weight is lower than the other parts of the absorber 40 or the absorber core 40a does not exist, in the back waistline region 30.

It must be noted that the waist stretch unit 100 and the absorber 40 are configured to overlap in at least one part in the plan view of the open-type disposable diaper 10. Specifically, the waist stretch unit 100 is configured to overlap at least a part of the low rigidity region 110, in the plan view of the open-type disposable diaper 10.

Furthermore, the low rigidity region 110 is formed to extend up to the proximity of an end E3 at the side of the back waistline region 30 in the product longitudinal direction L of the absorber 40.

The width of the low rigidity region 110 in the product widthwise direction W widens towards the end E3 at the side of the back waistline region 30 in the product longitudinal direction L of the absorber 40.

Additionally, the absorber 40 includes a stretch control region 120, which is the region where the stretch in the product widthwise direction W is more controlled than the other regions.

As illustrated in FIG. 2, the stretch control region 120 is formed at each of the outer sides in the product widthwise direction W of the low rigidity region 110.

More specifically, the low rigidity region 110 has a wedge shape in the plan view of the open-type disposable diaper 10.

Furthermore, the boundary between the stretch control region 120 and the low rigidity region 110 is formed in the shape of an arc such as a convex shape towards the center in the product widthwise direction W.

According to the above configuration, the wearing assistant can be made aware of the image of the shape of hip portion of the wearer.

As illustrated in FIG. 2, an end E4 at the side of the crotch region 25 in the product longitudinal direction L of the low rigidity region 110 may be arranged towards the crotch region 25 from a tape arrangement region 90A where the fastening tape 90 is provided.

An end E5 at the side of the back waistline region in the product longitudinal direction L of the waist stretch unit 100 may be arranged between the end E3 at the side of the back waistline region 30 in the product longitudinal direction L of the absorber 40 and the end E at the side of the back waistline region 30 in the product longitudinal direction L of the open-type disposable diaper 10.

Additionally, the end E2 at the side of the crotch region 25 in the product longitudinal direction L of the waist stretch unit 100 may either extend up to the end E4 at the side of the crotch region 25 in the product longitudinal direction L of the low rigidity region 110, or may run beyond the end E4 at the side of the crotch region 25 in the product longitudinal direction L of the low rigidity region 110.

Furthermore, as illustrated in FIG. 1, configuration may be such that a region D where the length of the absorber core 40a in the product widthwise direction W is the shortest may exist in the region where the crotch stretch unit 200a is arranged.

The open-type disposable diaper 10 is configured such that the crotch stretch unit 200a is the bottom portion of the open-type disposal diaper 10, and thus, the open-type disposable diaper 10 can be worn so as to run along the body of the wearer.

By providing the region D as described above, the bottom portion of the open-type disposable diaper 10 can be arranged more firmly on the crotch portion of the wearer.

Furthermore, as illustrated in FIG. 1, a central position O2 of the crotch stretch unit 200a in the product longitudinal direction L is configured to be arranged at the side of the front waistline region 20 from a central position O1 of the open-type disposable diaper 10 in the product longitudinal direction L.

In the region of rise from the crotch to the waist of the human body, the size at the hip side is larger than the size at the waist size. Therefore, according to the above configuration, the wearing assistant can easily put on the open-type disposable diaper 10 at an appropriate position based on the size of the rise from the crotch to the waist of the wearer.

In addition, as illustrated in FIG. 2, the length W1 in the product widthwise direction W in the central position O2 of the crotch stretch unit 200a in the product longitudinal direction L may be configured to be shorter than the length W2 in the product widthwise direction W at the ends of the crotch stretch unit 200a in the product longitudinal direction L.

According to the above configuration, because the shape of the crotch stretch unit 200a, as seen from the outside, appears to be constricted in the same manner as the crotch unit of a ladies underwear, when the wearing assistant puts the open-type disposable diaper 10 on the wearer, the diaper is worn such that the crotch stretch unit 200a is arranged on the crotch portion of the wearer, and it can be visually confirmed that the diaper has been worn at the correct position.

Figure 5:
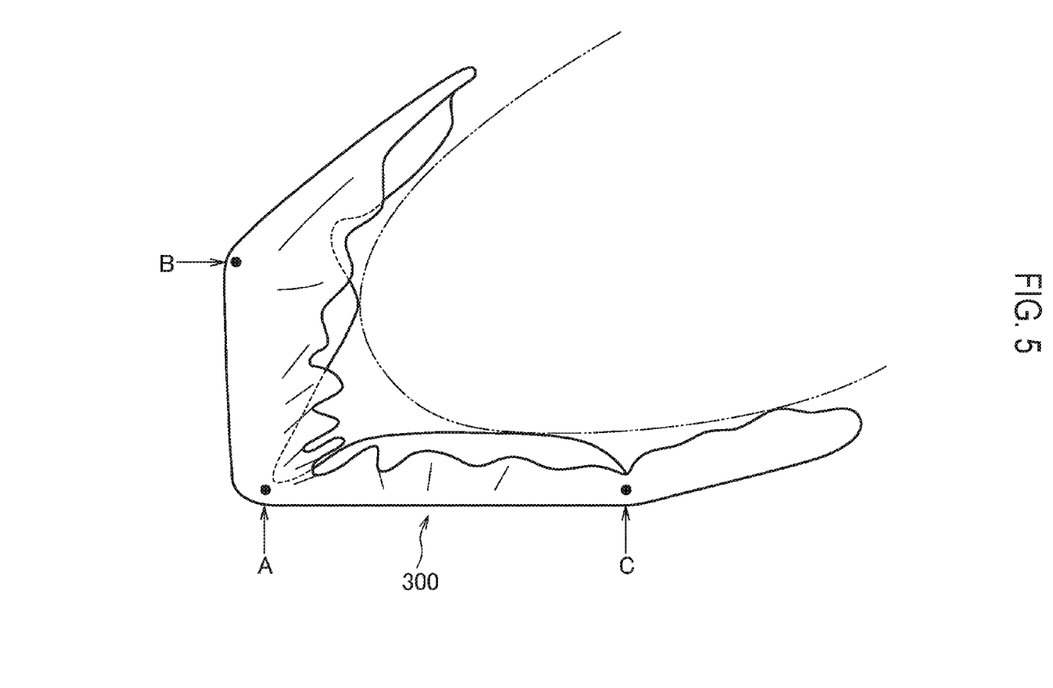
FIG. 5 is a diagram illustrating a state in which the open-type disposable diaper according to the first embodiment of the present invention is worn by the wearer.

Next, with reference to FIG. 4 through FIG. 6, the method in which the open-type disposable diaper 10 is worn by the wearer is explained.

Firstly, when the open-type disposable diaper 10 is taken out from the package and the open-type disposable diaper 10 that has been taken out is expanded, as illustrated in FIG. 4 and FIG. 6, in the natural state, the crotch region 25 rises up with the region A along the ends in the product longitudinal direction L at the side of the back waistline region 30 of the crotch stretch unit 200a, and the region B along the ends in the product longitudinal direction L at the side of the front waistline region 20 of the crotch stretch unit 200a as the base points.

Furthermore, in such a case, as illustrated in FIG. 4 and FIG. 6, a part of the back waistline region 30 rises towards the side of the crotch region 25 in the product longitudinal direction L with the region C between the end E1 at the side of the back waistline region 30 in the product longitudinal direction L of the leg stretch units 75, and the end E2 at the side of the crotch region 25 in the product longitudinal direction L of the waist stretch unit 100 as the base point.

It must be noted that because the absorber core arrangement region 300 is formed so as not to stretch, the absorber core arrangement region 300 is maintained in a state close to the plane surface without rising.

Secondly, as illustrated in FIG. 4 and FIG. 6, the wearing assistant (for example, the mother) makes the wearer lie down on an expanded open-type disposable diaper 10 so as to bring the dorsal portion of the wearer in contact with a part of the back waistline region 30 that is rising, and bring the hip portion of the wearer in contact with the absorber core arrangement region 300 between the rising crotch region 25 and the rising back waistline region 30.

The wearing assistant can be made aware of the image of a groove in the hip portion of the wearer by the wedge shape of the boundary between the stretch control region 120 and the low rigidity region 110, and therefore, as described above, the wearing assistant can understand through sensory perception that the groove in the hip portion of the wearer must be placed close to the boundary between the stretch control region 120 and the low rigidity region 110 in the expanded open-type disposable diaper 10 in the natural state.

Thirdly, after making the wearer lie down on the expanded open-type disposable diaper 10 in the natural state, as illustrated in FIG. 5, by folding back the front waistline region 20 and attaching the front waistline region 20 and the back waistline region 30 with the fastening tape 90, the open-type disposable diaper 10 is worn on the body of the wearer.

According to the open-type disposable diaper 10 of the present embodiment, when the open-type disposable diaper 10 is expanded, as illustrated in FIG. 4 and FIG. 6, in the natural state, the crotch region 25 rises with the region A and region B as the base points, a part of the back waistline region 30 rises towards the side of the crotch region 25 in the product longitudinal direction L with the region C as the base point, and the absorber core arrangement region 300 is maintained in a state close to the plane surface, because of which the wearing assistant can bring the dorsal portion of the wearer in contact with a part of the back waistline region 30 that is rising, and bring the hip portion of the wearer in contact with the region between the rising crotch region 25 and the absorber core arrangement region 300, which enables the wearing assistant to wear the open-type disposable diaper 10 on the wearer in the correct manner.

Furthermore, according to the open-type disposable diaper 10 of the present embodiment, by seeing the appearance of wrinkles in the crotch stretch unit 200a, when putting the open-type disposable diaper 10 on the wearer, the wearing assistant can lift up the disposable diaper while confirming visually that the crotch stretch unit 200a is appropriately arranged on the crotch portion of the wearer.

That is, when the wearing assistant realizes that the crotch stretch unit 200a is not arranged appropriately on the crotch portion of the wearer, the wearing assistant can adjust the position of wearing the open-type disposable diaper 10 before fixing the fastening tape.

As described above, according to the open-type disposable diaper 10 of the present embodiment, because the wearing assistant can easily wear the open-type disposable diaper 10 at the correct position on the wearer, the induction of leakage due to shifting of the position of wearing the open-type disposable diaper 10 can be avoided.

It must be noted that the open-type disposable diaper 10 according to the aforementioned characteristics of the present embodiment may be expressed as below.

The open-type disposable diaper 10 according to a characteristic of the present embodiment is summarized in configuration such that when the disposable diaper is expanded, then in the natural state, at least a part of the back waistline region 30 rises towards the side of the crotch region 25 in the product longitudinal direction L, the crotch region 25 curves towards the side of the back waistline region 30 in the product longitudinal direction L, and the front waistline region 20 curves towards the side opposite the side of the back waistline region 30 in the product longitudinal direction L.

Thus, the present invention has been explained in detail by using the above-mentioned embodiments; however, it is obvious that for persons skilled in the art, the present invention is not limited to the embodiments explained herein. The present invention can be implemented as corrected and modified modes without departing from the gist and the scope of the present invention defined by the claims. Therefore, the description of the specification is intended for explaining the example only and does not impose any limited meaning to the present invention.

In addition, the entire content of Japanese Patent Application No. 2012-024547 (filed on Feb. 7, 2012) is incorporated in the present specification by reference.

INDUSTRIAL APPLICABILITY

It is possible to provide an open-type disposable diaper that can be easily and correctly worn by a wearer.

The invention claimed is:

1. An open-type disposable diaper comprising:
a backsheet;
a front waistline region;
a back waistline region;
a crotch region positioned between the front waistline region and the back waistline region;
a pair of leg hole openings;
an absorber spanning the crotch region and extending to the front waistline region and back waistline region, the absorber including an absorber core;
a product longitudinal direction from the front waistline region towards the back waistline region;
a product widthwise direction perpendicular to the product longitudinal direction;
a crotch stretch unit arranged in the crotch region between the absorber and the backsheet and being stretchable in the product longitudinal direction;
a pair of leg stretch units formed along the leg hole openings and being stretchable in at least the product longitudinal direction; and
a waist stretch unit formed in the back waistline region and being stretchable in the product widthwise direction;
wherein, in a plan view of the open-type disposable diaper,
the absorber has an absorber core arrangement region where the absorber core is arranged,
the absorber core arrangement region is enclosed by the crotch stretch unit, the leg stretch units, and the waist stretch unit, and is not stretchable,
a length of the absorber core arrangement region in the product longitudinal direction is longer than a half of a length of the crotch stretch unit in the product longitudinal direction,
the absorber includes, in the back waistline region, a first low rigidity region where a basis weight is lower than a remaining region of the absorber or where the absorber core is not arranged,
the waist stretch unit has a region overlapping the first low rigidity region,
a dimension of the first low rigidity region in the product widthwise direction gradually increases away from the crotch stretch unit in the product longitudinal direction,
the absorber further includes, in the crotch region, a second low rigidity region and a third low rigidity region,
the crotch stretch unit has opposing ends in the product longitudinal direction, and
the second and third low rigidity regions extend in the product widthwise direction along the opposing ends of the crotch stretch unit.

2. The open-type disposable diaper according to claim 1, wherein in the plan view of the open-type disposable diaper,
the leg stretch units have ends at the back waistline region, and
the waist stretch unit has an end located closer to the front waistline region than the ends of the leg stretch units in the product longitudinal direction.

3. The open-type disposable diaper according to claim 1, wherein in the plan view of the open-type disposable diaper,
the absorber further includes a stretch control region arranged on opposite sides of the first low rigidity region in the product widthwise direction.

4. The open-type disposable diaper according to claim 3, wherein in the plan view of the open-type disposable diaper,
the first low rigidity region has a wedge shape, and
a boundary between the stretch control region and the first low rigidity region is formed in a shape of an arc convex towards a center of the absorber in the product widthwise direction.

5. The open-type disposable diaper according to claim 1, wherein in the plan view of the open-type disposable diaper,
the absorber has a region where a dimension of the absorber core in the product widthwise direction is the shortest, and
the crotch stretch unit is arranged in said region of the absorber core.

6. The open-type disposable diaper according to claim 1, wherein in the plan view of the open-type disposable diaper,
a central position of the crotch stretch unit in the product longitudinal direction is arranged between the front waistline region and a central position of the open-type disposable diaper in the product longitudinal direction.

7. The open-type disposable diaper according to claim 6, wherein in the plan view of the open-type disposable diaper,
a dimension of the crotch stretch unit in the product widthwise direction at the central position of the crotch stretch unit is shorter than a dimension of the crotch stretch unit in the product widthwise direction at the ends of the crotch stretch unit.

8. The open-type disposable diaper according to claim 1, wherein when the open-type disposable diaper is expanded and in a natural state,
at least a part of the back waistline region rises towards the crotch region in the product longitudinal direction,
the crotch region curves towards the back waistline region in the product longitudinal direction, and
the front waistline region curves away from the back waistline region in the product longitudinal direction.

9. The open-type disposable diaper according to claim 1, wherein in the plan view of the open-type disposable diaper,
the absorber includes opposite edges in the product widthwise direction, and
the second and third low rigidity regions extend all the way to the opposite edges of the absorber in the product widthwise direction.

10. The open-type disposable diaper according to claim 9, wherein in the plan view of the open-type disposable diaper,
the second low rigidity region is located between the crotch stretch unit and the back waistline region, and has a convex shape convex toward the back waistline region, and
the third low rigidity region is located between the crotch stretch unit and the front waistline region, and has a convex shape convex toward the front waistline region.

* * * * *